(12) United States Patent
Wutzler et al.

(10) Patent No.: US 9,790,225 B2
(45) Date of Patent: Oct. 17, 2017

(54) 4-AMINO-3-PHENYLAMINO-6-PHENYLPYRAZOLO[3,4-D]PYRIMIDINE DERIVATIVES, THEIR MANUFACTURE AND THEIR USE AS ANTIVIRAL ACTIVE SUBSTANCES

(71) Applicants: Peter Wutzler, Erfurt-Windischholzhausen (DE); Michaela Schmidtke, Jena (DE); Vadim Makarov, Moskau (RU)

(72) Inventors: Peter Wutzler, Erfurt-Windischholzhausen (DE); Michaela Schmidtke, Jena (DE); Vadim Makarov, Moskau (RU)

(73) Assignee: Scandion Oncology A/S, Copenhagen (DK)

( * ) Notice: Subject to any disclaimer, the term of this patent is extended or adjusted under 35 U.S.C. 154(b) by 106 days.

(21) Appl. No.: 14/350,885

(22) PCT Filed: Oct. 15, 2012

(86) PCT No.: PCT/EP2012/070403
§ 371 (c)(1),
(2) Date: Apr. 10, 2014

(87) PCT Pub. No.: WO2013/053942
PCT Pub. Date: Apr. 18, 2013

(65) Prior Publication Data
US 2014/0296259 A1    Oct. 2, 2014

(30) Foreign Application Priority Data

Oct. 14, 2011    (DE) .................... 10 2011 116 373
Oct. 20, 2011    (DE) .................... 10 2011 116 384

(51) Int. Cl.
*C07D 487/04*    (2006.01)
*A61K 31/519*    (2006.01)
*A61P 31/16*    (2006.01)
*A61K 45/06*    (2006.01)

(52) U.S. Cl.
CPC .......... *C07D 487/04* (2013.01); *A61K 31/519* (2013.01); *A61K 45/06* (2013.01)

(58) Field of Classification Search
CPC .................... C07D 487/04; A61K 31/519
See application file for complete search history.

(56) References Cited

FOREIGN PATENT DOCUMENTS

| WO | WO 94/13677 A1 | 6/1994 |
| WO | WO 00/43394 A1 | 7/2000 |
| WO | WO 2007/147401 A1 | 12/2007 |

OTHER PUBLICATIONS

Hansch et al., "A Survey of Hammett Substituent Constants and Resonance and Field Parameters", in Chem. Rev. 1991. 91, 165-195.*
International Preliminary Report on Patentability (IPRP) for International Application No. PCT/EP2012/070403, dated Apr. 24, 2014.
Tsuno, Yuho, "Hammett Equation", Yuki Gosei Kagaku Kyokai, 1965 23(8), pp. 631-642.
Office Action corresponding to Japanese Application No. 2014-535117 dated Apr. 22, 2016.
Perrin, D. D. et al., "pka Prediction for Organic Acids and Bases", Chapman & Hall, London, 1981, ISBN 978-94-009-5885-2, Appendix pp. 109-139.
Patent Examination Report No. 2 corresponding to Australian Application No. 2012322750 dated May 4, 2016.

* cited by examiner

*Primary Examiner* — Susanna Moore
(74) *Attorney, Agent, or Firm* — Myers Bigel, P.A.

(57) ABSTRACT

The present invention relates to 5-amino-3-phenylamino-6-phenylpyrazolo[3,4-d]pyrimidine derivatives of the general formula I

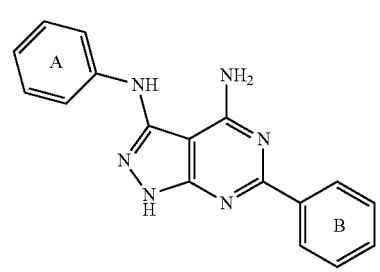

or pharmaceutically acceptable salts or propharmacons thereof, wherein at least one hydrogen atom in at least one of the phenyl groups A and B is substituted by a substituent $R^H$, which has a Hammett constant $\sigma_p$ greater than 0.23. The present invention also concerns the method of its manufacture. For corresponding compounds, surprisingly a particularly high activity against viruses, in particular rhinoviruses and picornaviruses was determined. Furthermore, the compounds are tolerated very well. For these reasons the compounds are suitable for the treatment of viral infections and as drugs.

14 Claims, No Drawings

4-AMINO-3-PHENYLAMINO-6-PHENYLPYRAZOLO[3,4-D]PYRIMIDINE DERIVATIVES, THEIR MANUFACTURE AND THEIR USE AS ANTIVIRAL ACTIVE SUBSTANCES

This application is a 35 U.S.C. §371 national phase application of PCT Application PCT/EP2012/070403, filed Oct. 15, 2012, which claims priority to DE 102011116373.9, filed Oct. 14, 2011 and DE 102011116384.4, filed Oct. 20, 2011. The entire content of each of these applications is incorporated herein by reference.

The invention concerns new types of 4-amino-3-phenylamino-6-phenylpyrazolo[3,4-d]pyrimidine derivatives and their use as antiviral agents, preferably for the treatment of picornavirus infections.

Picornaviruses, especially enteroviruses and rhinoviruses, are responsible for a broad spectrum of diseases in humans. The enteroviruses include more than 60 different human pathogenic serotypes (Melnick J in: Fields B et al., editors. Virology. Philadelphia: Lippincott-Raven Publishers; 1996, 655-712). Enterovirus, echovirus, coxsackievirus A and B infections often take a course of nonspecific fever and cause diseases of the upper respiratory tract which frequently cannot be distinguished from rhinovirus infections. More serious clinical pictures which can also occur as epidemics, include hemorrhagic conjunctivitis, herpangina, hand-foot-and-mouth disease, aseptic meningitis, encephalitis and acute myocarditis. Thus different virus types can cause the same symptoms or one virus type can cause quite different clinical pictures. With the introduction of modern and sensitive methods in virus diagnostics persistent enteroviral RNA as well as virus proteins could be identified in connection with chronic diseases such as type 2 diabetes, poliomyositis and especially chronic myocarditis. Persistent enterovirus infections also occur in patients with agammaglobulinemia and present as persistent enterovirus meningoencephalitis. Dermatomyositis or polymyositis often occurred as attendant symptoms. The rhinoviruses include approx. 100 serotypes. Rhinovirus infections cause more than half of all respiratory diseases of the upper respiratory tract in humans (Couch R B in: Fields B M et al., editors: Fields Virology, 3rd edition. Lippincott-Raven, Philadelphia, 1996, 713-35). In an average duration of the disease of approx. 10 days these colds which take a mostly harmless course lead to millions of GP visits and time off school and work each year. Possible complications include otitis media, sinusitis, exacerbation of asthma and cystic fibrosis as well as infections of the lower respiratory tract especially in young children, older patients and immuno-suppressed patients. Because of the variety of types prophylactic vaccination is currently not possible. As a result of the working days lost, GP visits and medicines associated with these illnesses rhinoviruses and enteroviruses mean significant costs annually. The treatment of these viral infections to date has depended on symptoms as there are no virus-specific therapeutic agents available (Rotbart H A: Antiviral Res 2002, 53(2), 83-98). In addition, antibiotics are often prescribed unnecessarily. The development of new virustatic agents is therefore absolutely essential.

The results of the intensive search for potential treatments for enterovirus and rhinovirus infections were summarised by Rotbart in 2002 in an overview article (Rotbart H A: Antiviral Res 2002, 53(2), 83-98). For example, ribavirin inhibits a host cell enzyme, the inosine 5'-monophosphate (IMP) dehydrogenase. By deactivating this key enzyme for the synthesis of purine nucleotides, the replication of picornaviruses is inhibited in vitro and in viva. Furthermore, ribavirin is to be inserted directly into the genome of polio viruses and thereby also act as a mutagen for RNA viruses (Crotty S et al.: Nat Med, 2000, 6(12), 1375-9). Because of serious side effects these compounds are not used to treat rhinovirus and enterovirus infections. Specific targets to prevent viral RNA synthesis are the genome itself, the viral RNA-dependent RNA polymerase as well as other viral proteins necessary for the replication complex. Guanidines, thiosemicarbazones, benzimidazoles, dipyridamoles and flavones have been known for a long time as inhibitors of the polymerases of different picornaviruses in the cell culture. Varying degrees of success were thereby achieved in vivo. Enviroxime derivatives are deemed to be the most promising candidate with broad anti-enterovirus and anti-rhinovirus activity. Enviroxime impedes the synthesis of plus strand RNA by binding to the virus protein 3A, which is necessary for the formation of RNA intermediates in virus reproduction (Heinz B A and Vance L M: J Virol, 1995, 69(7), 4189-97). In clinical studies moderate or no therapeutic effects, poor pharmacokinetics and undesirable side effects were observed (Miller F D et al.: Antimicrob Agents Chemother, 1985, 27(1), 102-6). To date there is no clinical data available for newer derivatives with better bioavailability and tolerance.

Based on the knowledge of the fine structure and function of the viral protease 2C the protease inhibitor AG 7088 was developed. AG 7088 acts in the cell culture in the nanomolar concentration range against 48 rhinovirus types as well as coxsackie virus A21, 63, enterovirus 70 and echovirus 11 (Pattick A K et al.: Antimicrobila Agents Chemother, 1999, 43(10), 2444-50). The concluding data of the clinical studies are not known to date.

With the clarification of the molecular structure of the viral capsids the prerequisites for a targeted design of capsid blockers, the "WIN substances" were created (Diana G D: Curr Med Chem 2003, 2, 1-12). They hinder the adsorption and/or the uncoating of rhinoviruses and enteroviruses. Some of the WIN substances only act extremely specifically against individual genus types or virus types of the picornaviruses. Other derivatives inhibit the replication of rhinoviruses as well as enteroviruses. The WIN substances include for example arildone, disoxaril and pirodavir. These compounds showed very good antiviral effects in the cell culture. Poor solubility (arildone), low bioavailability (arildone and disoxaril), fast metabolisation and excretion (disoxaril and WIN 54954) as well as side effects, for example skin rash (WIN 54954), made a clinical application impossible. Great hopes were placed on pleconaril, another capsid inhibitor. Pleconaril has a very good oral bioavailability and after binding to the hydrophobic pocket in the virus capsid inhibits the penetration of rhinoviruses, echoviruses and coxsackie viruses (Pevear D C et al.: Antimicrob Agents Chemother 1999, 43(9), 2109-15; McKinley M A et al.: Annu Rev Microbial 1992, 46, 635-54). Therefore it is potentially effective against a broad spectrum of viral diseases, from the common cold through to viral meningitis or myocarditis. Resistance was observed in the case of rhinoviruses, enterovirus 71 and coxsackie virus B3 (Ledford R M et al.: J Viral 2004, 78(7), 3663-74; Groarke J M et al.: J Infect Dis 1999, 179(6), 1538-41). Clinical studies of children and adults with enterovirus meningitis (Abzug M J et al.: Pediatr Infect Dis J, 2003, 22, 335-41) as well as respiratory infections caused by the rhinovirus (Hayden F G et al.: Antivir Ther, 2002, 7, 53-65; Hayden F G et al.: Clin Infect Dis, 2003, 36, 1523-32) went well. The proven therapeutic effect however is not sufficient for licensing pleconaril (Picovir, Viropharma, USA) to treat rhinovirus infections in the USA. In March 2002 a corresponding application was refused by the Food and Drug Administration: FDA on the grounds of an unfavourable risk-benefit assessment.

Pyrazolopyrimidines have also been described as CRF antagonists (Corticotropin-Releasing Factor Antagonists) (e.g. EP 674 642 and EP 691 128), which, for example, inhibit adenosine kinase (EP 496 617 or U.S. Pat. No. 4,904,666), xanthine oxigenase (J. Heterocyc. Chem. 19, 1565, 1982) or other enzyme systems (U.S. Pat. No. 2,965, 643 and U.S. Pat. No. 3,600,389).

Thus it continues to be a crucial part of antiviral research to develop highly effective antiviral agents to treat rhinovirus and enterovirus diseases. The new compounds should be well tolerated and overcome existing resistance, e.g. in the case of pleconaril.

WO 00/43394 A discloses substituted pyrazolo[3,4-d]pyrimidine derivatives and their use as antiviral agents.

EP 2 049 540 also discloses 4-amino-3-arylamino-6-arylpyrazolo[3,4-d]pyrimidine derivatives and their use as antiviral agents.

The purpose of the invention is to specify other pyrazolo[3,4-d]pyrimidine derivatives as well as their manufacture and use which can be used as antiviral agents against enteroviruses and rhinoviruses as well as avoid the stated disadvantages of the prior art, for example, with regard to the stability and bioavailability of the substances.

This purpose is met by specifically substituted 4-amino-3-phenylamino-6-phenylpyrazolo[3,4-d]pyrimidine derivatives of the general formula I, including their pharmaceutically tolerated salt compounds and their pro-pharmacons,

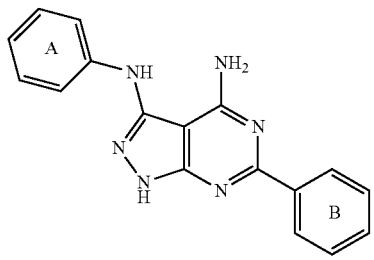

I wherein at least one hydrogen atom in at least one of the phenyl groups A and B is replaced by a substituent $R^H$, which has a Hammett constant $\sigma_p$ greater than 0.23,
wherein every further hydrogen atom in each of the phenyl groups A and B can be replaced independently of each other by a residue $R^1$, wherein
each $R^1$ independently can be a halogen, a saturated or unsaturated, linear or branched aliphatic radical with 1-7 chain members, a saturated or unsaturated, linear or branched alkanol radical with 1-8 chain members, $NO_2$, CN, $CONR^2_2$, $COR^2$, $COOR^2$, $OR^2$, $SR^2$, $NR^2_2$, $SO_2NR^2_2$, $CX_3$, $CR^2X_2$, $OCX_3$, $OCR^2X_2$, or phenyl;
each $R^2$ independently is hydrogen, a saturated or unsaturated, halogenated or non-halogenated, linear or branched aliphatic radical with 1-7 chain members, benzyl, phenyl or naphthyl, a saturated or unsaturated, mono- or polyheterocycle with the heteroatoms N, S or O, wherein each of the above-mentioned groups can be independently substituted with fluorine, chlorine, bromine, trifluoromethyl, alkyl, alkoxy, cyano, nitro, amino, aminoalkyl, C(O)-alkyl, C(O)O-alkyl, benzyl, phenyl or naphthyl; and X independently is F, Cl, Br, or I.

In the subclaims the advantage of the specifically substituted 4-amino-3-phenylamino-6-phenylpyrazolo[3,4-d]pyrimidine derivatives are explained as well as the potential applications, without limiting the invention in any way.

4-amino-3-phenylamino-6-phenylpyrazolo[3,4-d]pyrimidine derivatives of the general formula I are advantageous, wherein at least one hydrogen atom in at least one of the phenyl groups A and B is replaced by a substituent $R^H$, selected from $NO_2$, CN, $CF_3$, $CCl_3$, $CBr_3$, $OCF_3$, $OCCl_3$, $OCBr_3$, $CHF_2$, $CHCl_2$, $CHBr_2$, $OCHCl_2$, CHO, COON, COMe, COEt, COOMe or COOEt, preferably $CF_3$ or $OCF_3$. It is an advantage that in one or both phenyl groups A and B one, two or three hydrogen atoms are replaced by a substituent $R^H$. In a special embodiment precisely one hydrogen atom in one of the phenyl groups A and B is replaced by a substituent $R^H$. The substituent $R^H$ can be in para position of the phenyl ring A or B.

In addition to $R^H$ each of the phenyl groups A and B can independently of each other carry further residues $R^1$. It is an advantage that the phenyl groups A and B independently of each other carry none, one, two or three further residues $R^1$, preferring none or a further residue $R^1$.

As alkyls it is worth considering in connection with the invention in particular linear or branched $C_{1-7}$-alkyls, for example, methyl, ethyl, n-propyl, i-propyl and butyl. The same applies to alkanols, alkylamines and alkylamides in connection with the invention.

Covered by the invention are in particular 4-amino-3-phenylamino-6-phenylpyrazolo[3,4-d]pyrimidine derivatives of the general formula II

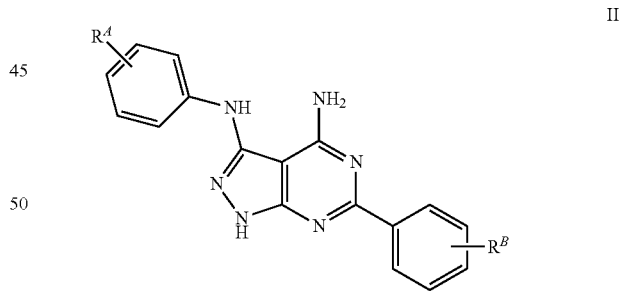

II wherein each substituent $R^A$, $R^B$ independently can be hydrogen, a halogen, a saturated or unsaturated, linear or branched aliphatic radical with 1-7 chain members, a saturated or unsaturated, linear or branched alkanol radical with 1-8 chain members, $NO_2$, CN, $CONR^2_2$, $COR^2$, $COOR^2$, $OR^2$, $SR^2$, $NR^2_2$, $SO_2NR^2_2$, $CX_3$, $CR^2X_2$, $OCX_3$, $OCR^2X_2$, or phenyl; and $R^2$ and X as defined above; wherein at least one of the substituents $R^A$, $R^B$ has a Hammett constant $\sigma_p$ greater than 0.23.

The invention includes in particular 4-amino-3-phenylamino-6-phenylpyrazolo[3,4-d]pyrimidine derivatives of the general formula IIa

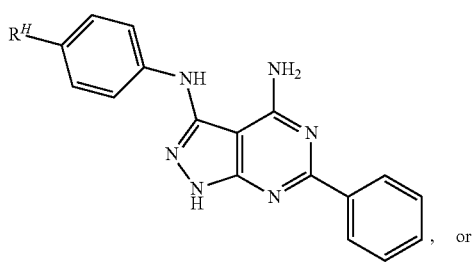

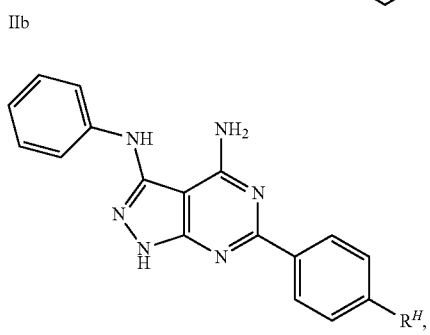

wherein $R^H$ is selected from $NO_2$, CN, $CF_3$, $CCl_3$, $CBr_3$, $OCF_3$, $OCCl_3$, $OCBr_3$, $CHF_2$, $CHCl_2$, $CHBr_2$, $OCHCl_2$, CHO, COON, COMe, COEt, COOMe or COOEt, preferably $CF_3$ or $OCF_3$.

Also included are pharmaceutical compositions, which contain a 4-Amino-3-phenylamino-6-phenylpyrazolo[3,4-d]pyrimidine derivative according to the general formulas I, II, IIa or IIb. Such pharmaceutical compositions can contain further substances, for example, pharmaceutically acceptable excipients and carriers. In a particular aspect the pharmaceutical compositions can include additional active ingredients, in particular antiviral agents, especially active agents against picornaviruses.

Surprisingly, it was shown that the 4-amino-3-phenylamino-6-phenylpyrazolo[3,4-d]pyrimidine derivatives in the invention have a significantly better stability in liver microsomes compared with the state-of-the-art substances.

Furthermore investigations on the pharmacokinetics in mice showed that the 4-amino-3-phenylamino-6-phenylpyrazolo[3,4-d]pyrimidine derivatives in the invention have a significantly better bioavailability than state-of-the-art substances. At the same time the compounds of the present invention show strong antiviral activity against picornaviruses, especially enteroviruses and rhinoviruses in the nano or micromolar concentration range.

Therefore the pharmaceutical preparations which contain a compound of the formulas I, II, IIa or IIb, are particularly suitable for the treatment of respiratory infections, aseptic meningitis, encephalitis, herpangina etc. in humans and animals, which can be caused by picornaviruses especially enteroviruses and rhinoviruses.

The 4-amino-3-phenylamino-6-phenylpyrazolo[3,4-d]pyrimidine derivatives are characterized by the fact that they carry at least one substituent $R^H$ on one or on both phenyl groups, which has a Hammett constant $\sigma_p$ greater than 0.23. This value 0.23 corresponds to the Hammett constant $\sigma_p$ of the bromine, which shows the highest Hammett constant for the para position among the halogens.

The determination of the Hammett constants for different substituents is based on the ionization constants of the benzoic acid according to the Hammett equation $$\sigma_x = \log K_X - \log K_H$$

wherein $K_H$ is the ionization constant for benzoic acid in water at 25° C. and $K_X$ is the corresponding constant for a meta or para substituted benzoic acid. A method to determine the Hammett constant for different substituents in meta ($\sigma_m$) and para position ($\sigma_p$) as well as values already ascertained of a variety of substituents can be taken from the publication of Hansch et al., "A Survey of Hammett Substituent Constants and Resonance and Field Parameters", in Chem. Rev. 1991. 91, 165-195, which is incorporated herein in its entirety. Of significance to this invention is thus exclusively the value a respectively for the para position ($\sigma_p$), irrespective of the position where at least one substituent $R^H$ is finally located.

Examples of the invention are compounds in Table 1, including their pharmaceutically tolerated salt compounds.

TABLE 1

| Compound | Formula | Solvent for crystallisation | Melting point °C. | Molecular formula | MS EI (m/z) (M⁺) | Analysis Calculated (B) % Found (G) % | ¹H NMR (DMSO-d₆) δ, ppm |
|---|---|---|---|---|---|---|---|
| CRCV-340 | | THF, Toluene | — | $C_{18}H_{13}F_3N_6$ | 370.3312 | B: C 58.3; H 3.54; N 22.69 | — |

TABLE 1-continued

| Compound | Formula | Solvent for crystallisation | Melting point °C. | Molecular formula | MS EI (m/z) (M+) | Analysis Calculated (B) % Found (G) % | 1H NMR (DMSO-d6) δ, ppm |
|---|---|---|---|---|---|---|---|
| MS-112 | | EtOH | — | $C_{18}H_{13}F_3N_6O$ | 386.3306 | B: C 55.96; H 3.39; N 21.75 | — |
| MS-115 | | DMF/EtOH | 272-74 | $C_{19}H_{11}ClF_6N_6$ | 472.7831 | B: C 48.27; H 2.35; N 17.78 G: C 48.31; H 2.50; N 17.64 | — |
| MS-116 | | Activated carbon, EtOH | 271-73 | $C_{18}H_{12}ClF_3N_6$ | 404.7847 | B: C 53.41; H 2.99; N 20.76 G: C 53.49; H 3.14; N 20.61 | 13.10 (1H, br.s., NH), 8.84 (1H, d, CH), 8.55 (1H, br.s., NH), 7.10-8.02 (9H, br.m, NH2, 7CH) |
| MS-117 | | EtOH | 230-32 | $C_{18}H_{13}F_3N_6$ | 370.3397 | B: C 58.38; H 3.54; N 22.69 G: C 58.61; H 3.67; N 22.45 | — |

Also covered are pro pharmacons (prodrugs) of the compounds, especially those which are characterized by a substituent on the pyrazol heteroatom in position 1. It has been shown that such types of compounds are converted in vivo to the 1H pyrazol compound. As an example, compounds have been mentioned in respect of which the pyrazol heteroatom in position 1 is substituted by an imino(phenyl) methyl substituent, such as, for example, 1-[Imino(phenyl) methyl]-4-amino-3-(4-trifluormethyl-phenyl)amino-6-phenylpyrazolo[3,4-d]pyrimidine, also designated by the IUPAC name 1-benzylcarboximidoyl-6-phenyl-3-N-[4-(trifluormethyl)phenyl]-1H-pyrazolo[3,4-d]-pyrimidine-3,4-diamine. Here this relates to a by-product of the manufacture of the compound described above, CRCV-340, resulting from the reaction of the compound CRCV-340 with an excess of benzamidine in the reaction mixture and having the following formula:

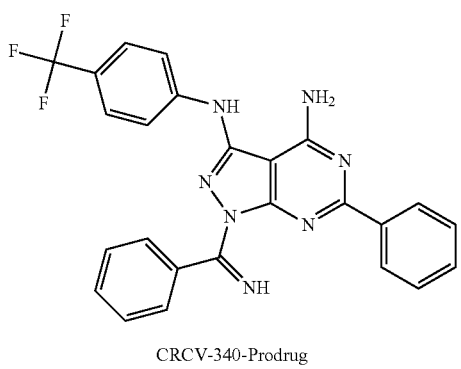 [SMILES: N=C(c1ccccc1)n1nc(Nc2ccc(C(F)(F)F)cc2)c2c(N)nc(-c3ccccc3)nc21]

CRCV-340-Prodrug

It was found that these compounds (e.g. CRCV-340 prodrug) in vivo are very easily converted into the target compound in such a way that in the serum only the final active ingredient (e.g. CRCV-340) can mainly be proven. Also included are the salts, solvates or solvates of the salts produced by the above compounds. Within the scope of this invention the preferred salts are physiologically harmless salts of the compounds relating to the invention. Physiologically harmless salts of the compound relating to the invention include addition salts of mineral acids, carboxylic acids and sulphonic acids, e.g. salts from hydrochloric acid, hydrobromic acid, sulphuric acid, phosphaic acid, methane sulphonic acid, sulphonic acetic acid, toluene sulphonic acid, benzenesulphonic acid, naphthalene-sulphonic acid, acetic acid, trifluoroacetic acid, propionic acid, lactic acid, tartaric acid, malic acid, citric acid, fumaric acid, maleic acid and benzoic acid.

The invention shall be explained below in more detail using synthesising methods, special 4-amino-3-phenylamino-6-phenylpyrazolo[3,4-d]pyrimidine derivatives of the general formula (I) as well as their effect and use against picornavirus infections.

Fig. 1 shows a general diagram on the synthesis of pyrazolo[3,4-d]pyrimidine 1 and includes in the first step the condensation of [bis(methylthio)methylen]malononitril 2 with phenylamines 3 in alcohol to phenyl derivatives 4. The latter can be isolated respectively and purified for further reactions or used directly without purification for subsequent reactions ("one-pot" reaction). The subsequent step constitutes the interaction of the phenyl derivative 4 with hydrazine or hydrazine derivatives. The reaction takes place by boiling for 1 to 4 hours and leads to a high yield of pyrazol 5. The final step of the synthesis of pyrazolo[3,4-d]pyrimidine 1 is the condensation of the pyrazol 5 with phenylamidine 6 in the presence of acetic acid, trifluoroacetic acid or sodium acetate.

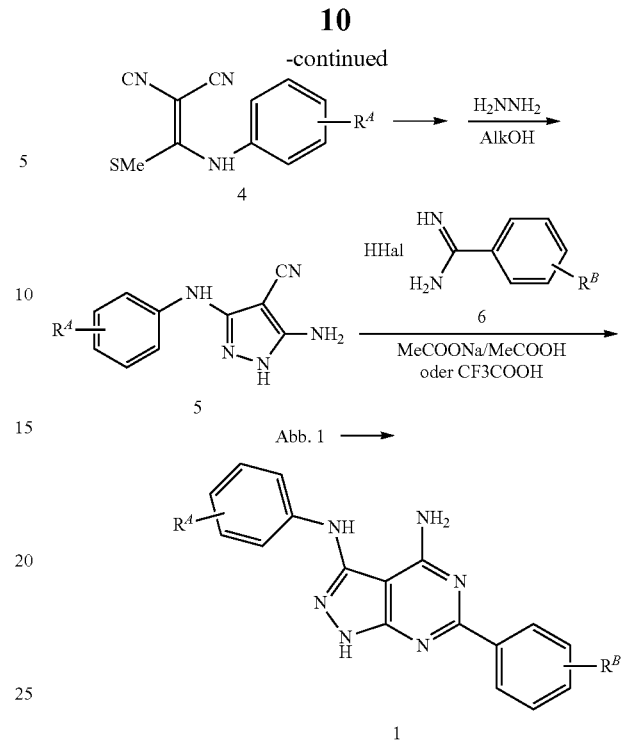

Abb. 1 →

The compounds can be thereby obtained advantageously by transforming the pyrazol (5) in the last synthesis step with corresponding benzamidine hydrochloride in the presence of an excess of sodium acetate at 200-220 in the absence of solvents.

Alternatively the compounds can be obtained by converting the pyrazol (5) in the last synthesis step with corresponding benzonitrile (a large surplus) with microwave irradiation and in the presence of potassium-tert-butylate.

An alternative synthesis method is the "one-pot" reaction of malononitrile with aryl isothiocyanates in the presence of sodium hydride and a subsequent treatment of the reaction mixture with methyl iodide or dimethyl sulphate. In the process large amounts of enamine are produced. Here too the condensation of pyrazol 5 with arylamidines 6 in the presence of acid, such as acetic acid or trifluoroacetic acid, or their salts (acetate) is again the final synthesis step to produce pyrazolo[3,4-d]pyrimidine 1.

It has been shown that the conversion of the pyrazol (5) to pyrazolo[3,4-d]pyrimidine with particularly high yields can be done by using the benzamidine components as a free base and the reaction is carried out in polar solvents. An advantage of this method is also that the proportion of byproducts which are difficult to separate can be minimised. This reaction can be effected, based on substituted 5-amino-4-cyano-3-phenylamino-pyrazoles (5) with optional substituted benzamidines as a free base (6) to 4-amino-3-(phenylamino)-6-phenylpyrazolo[3,4-d]pyrimidine (1) according to the following reaction diagram.

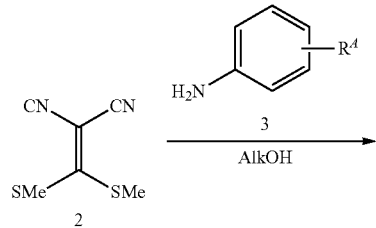

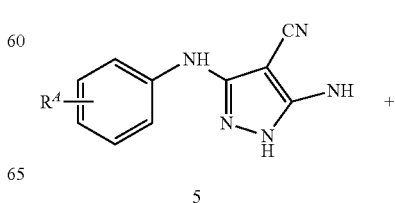

FIG. 2

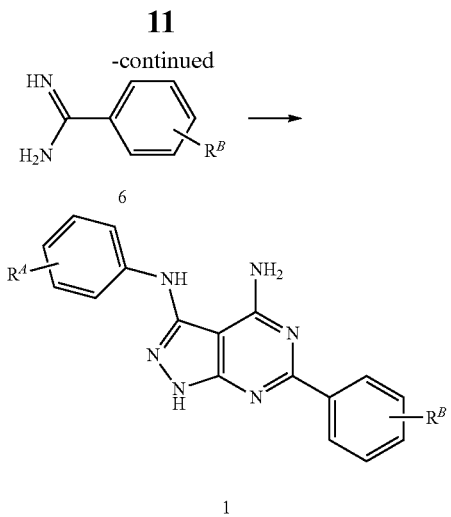

The residues $R^A$ and $R^B$ are substituents, as defined above for $R^1$.

Whilst the conversion described above is particularly suitable for the manufacture of 4-amino-3-phenylamino-6-phenylpyrazolo[3,4-d]pyrimidine derivatives of the above general formula (I), wherein at least one hydrogen atom in at least one of the phenyl groups A and B is replaced by a substituent $R^H$, which has a Hammett constant $\sigma_p > 0.23$, the method can also [be used?][1] for the manufacture of 4-amino-3-phenylamino-6-phenylpyrazolo[3,4-d]pyrimidines, which have no such substituents, i.e. in which this residue represents hydrogen or a residue $R^1$, as defined above in connection with formula I.

[1] Translator's note: The verb is missing in the original German; "be used" is appropriate in this context.

Preferably the present invention also concerns reactions, as described above, in which the residues $R^A$ and $R^B$ independently of each other can be selected from $NO_2$, CN, $CONR^3_2$, $COOR^3$, CHO, $CHONH_2$, a halogen, an unsaturated or saturated linear or branched aliphatic radical (called alkyl group) with 1 to 6 chain members, a saturated or unsaturated linear or branched alkanol radical (also called alkoxy group) with 1 to 6 chain members, $OR^3$, $SR^3$, $NR^3_2$, $SO_2NR^3$, di- or trifluoromethyl and the residue $R^3$ can consist of H, methyl-, ethyl-, propyl- or butyl-groups. Insofar as the compounds of the invention can exist in tautomeric forms, the present invention comprises all tautomeric forms.

The substituents in the paragraph above have the following meaning insofar as nothing is specified to the contrary:

Alkyl as well as the alkyl parts in alkoxy stand for straight-chain or branched alkyls and comprise, if nothing to the contrary is stated, (C1-C6)-alkyl, especially (C1-C4)-alkyl, e.g. methyl, ethyl, propyl, isopropyl, butyl, isobutyl. Advantageously alkoxy stands for a straight-chain or branched alkoxy residue, especially with 1 to 6, in particular preferably 1 to 4 and mostly preferably 1 to 3 carbon atoms. As an example and as a preference methoxy, ethoxy, N-propoxy, isopropoxy, t-butoxy, n-pentoxy and n-hexoxy are mentioned. Aryl stands for a mono- to tricyclic aromatic, carbocyclic residue generally with 6 to 14 carbon atoms. As an example and as a preference aryl is selected from phenyl, naphthyl and phenantrenyl, in particular phenyl is preferred. Halogen stands for fluorine, chlorine, bromine and iodine, preferably fluorine and chlorine.

It is also possible with this method to manufacture general arylpyrazolo[3,4d]pyrimidine derivatives, wherein in this case the phenylamidine 6 is to be replaced by a corresponding arylamidine. In particular instead of phenyl rings A and B also naphthyl, pyridyl, chinolyl, pyrazinyl, pyrimidyl, pyrazolyl, triazinyl, imidazolyl, furanyl, thienyl can be contained in the end product, wherein each hydrogen atom in each of the above-mentioned group independently of each other can be replaced by a residue $R^1$, as defined above in connection with the formula I. Such a method is also the subject-matter of this invention.

The reaction shown in Fig. 2 is effected in inert, polar organic solvents. Inert polar organic solvents are, for example, ether such as diethylether, methyl-tert.-butylether, 1,2-dimethoxyethane, glycol diethyl ether or diethylene glycol dimethyl ether, cyclic ether, such as dioxane, tetrahydrofuran, hydrocarbons, such as ethyl benzene, xylene, toluene or alcohols, such as ethanol, propanol, butanol, isobutanol and isopropanol. Particularly pure products are obtained by using n-butanol as a solvent. n-butanol should be used in a molar ratio of 1 to 10, in particular preferably 1.5 to 3, in relation to the initial value of the pyrazole derivative.

Within the scope of the present invention it emerged as particularly useful if the benzamidine (6) is freshly prepared in basic form (as free base). The synthesis is effected using the usual methods from the correspondingly available salt. It is best to use benzamidine (6) in a molar ratio of 1 to 1.5, based on the pyrazole derivatives (5).

The reaction is carried out at a temperature from 60 to 110° C., preferably 85 to 95° C., over 10-30 hours, preferably 18-20 hours.

The amino-3-(phenylamino)-6-phenylpyrazolo[3,4-d]pyrimidine (1) obtained in this way is cleaned by recrystallization. For this preferably tetrahydrofuran or a mixture of tetrahydrofuran with water or an organic solvent is used, in particular preferably with toluene. Alternatively to that the amino-3-(phenylamino)-6-phenylpyrazolo[3,4-d]pyrimidine can also be cleaned by precipitation from a hot solution in tetrahydrofuran with water or an organic solvent, preferably with toluene.

In the following examples special compounds of the general formula (I) are listed, which are suitable preferably for applications against picornavirus infections, wherein the compounds can be prepared in a solution or a suspension in a pharmaceutically acceptable aqueous, organic or aqueous-organic medium for the local or parenteral application by intravenous, subcutaneous or intramuscular injection or for intranasal administration, or developed in the form of a tablet, capsule or aqueous suspension with a conventional carrier for oral administration or as a suppository.

The compounds presented in the formula (I) can thus be used in doses of 0.1 to 1000 mg/kg body weight.

Manufacture and Analysis of the 4-amino-3-phenylamino-6-phenylpyrazolo[3,4-d]pyrimidine Derivatives The structural clarification of the compounds of the invention is effected by the type of synthesis, elementary analyses, NMR spectroscopy and mass spectrometry.

Source Materials:

The 5-amino-4-cyano-3-phenylaminopyrazoles were synthesised according to the method shown in Fig. 1 as well as according to the description of Tominaga Y et al. (J. Heterocycl. Chem., 1990, 27, 775-779). Arylamidines are synthesised according to the known prior art from the corresponding cyanogen source compounds (Boere, R T et al.: J. Organomet. Chem., 1987, 331, 161-167; Garigipati R S: Tetrahedron Lett., 1990, 31, 1969-1978; Dann O et al.: Justus Liebigs Ann. Chem., 1982, 1836-1839).

REFERENCE EXAMPLE 1

4-amino-3-phenylamino-6-phenylpyrazolo[3,4-d]pyrimidine 3-N,6-diphenyl-2H-pyrazolo[3,4-d]pyrimidine-3,4-diamine 3.0 g (17.24 mmol) benzamidin hydrochloride hydrate and 2.2 g (23.0 mmol) sodium acetate are added to 2.3 g (11.5 mmol) 5-amino-4-cyano-3-phenylaminopyrazol whilst stirring. The reaction mixture is heated for 30 min at 220° C. The resulting material is treated with 50 ml water, filtered and washed with 20 ml cold methanol and 20 ml cold ester. The product is cleaned by means of crystallisation from DMF/water.

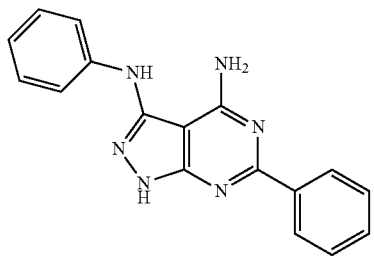

Light yellow, solid crystalline material. Yield 57%. mp 253-5° C. $R_f$(chloroform-methanol; 10/1)-0.8 (silica gel 60). MS m/z 302 (M+).

REFERENCE EXAMPLE 2

4-amino-3-(phenylamino)-6-phenylpyrazolo[3,4-d]pyrimidine (alternative manufacture)

5.22 g benzamidine hydrochloride, previously dried for 2.5 hr at 115° C., is slowly added to a solution of 1.74 g sodium methylate in 100 ml methanol and stirred for 30 min at room temperature. After filtering out the anorganic white precipitation 3.5 ml n-butanol is added and the volume reduced in the vacuum to 3 ml. The residue is a whitish oil, and corresponds to 4.0 g benzamidine, which is used immediately in the next reaction step.

5-amino-4-cyano-3-(phenylamino)-pyrazol (6.0 g; powder Ref-1) is dissolved in 10 ml n-butanol and 4.0 g benzamidine in 3 ml n-butanol added at room temperature. The reaction takes place over 20 hours at 85° C. Finally, the solution is cooled, the yellow precipitation filtered out and washed with 5 ml n-butanol and 5 ml toluene.

Yield: 68%

Properties: Melting point: 265-267° C. (tetrahydrofuran); MS (m/z) 302 (M+); $^1$H NMR (DMSO-$d_6$); δ 12.38 (1H, s, NH), 8.30-8.36 (2H, q, 2CH), 8.23 (1H, br, s., NH), 7.67 (2H, d, 2CH), 7.48 (2H, br. s., NH$_2$), 7.42 (3H, m, 3CH), 7.12 (2H, d, 2CH) and 6.98 (1H, m, CH) ppm; Elementary analysis $C_{17}H_{14}N_6$: Calculated %: C, 67.54; H, 4.67; N, 27.80. Found %: C, 67.49; H, 4.53; N, 27.74.

REFERENCE EXAMPLE 3

4-amino-3-(4-chlorphenyl)amino-6-phenylpyrazolo[3,4-d]pyrimidine (3-N-(4-chlorphenyl)-6-phenyl-2H-pyrazolo[3,4-d]pyrimidine-3,4-diamine)

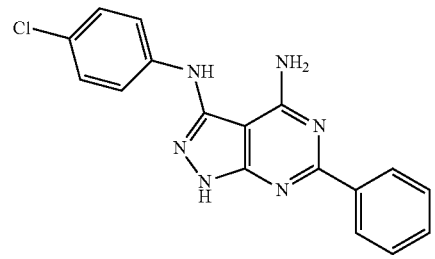

REFERENCE EXAMPLE 4

4-amino-3-(3,4-difluorphenyl)amino-6-phenylpyrazolo[3,4-d]pyrimidine (3-N-(3,4-difluorphenyl)-6-phenyl-2H-pyrazolo[3,4-d]pyrimidine-3,4-diamine)

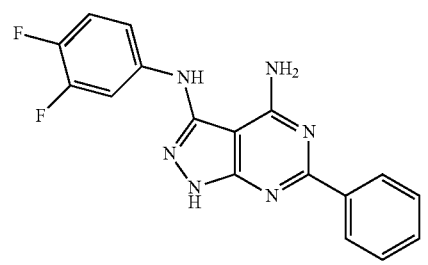

REFERENCE EXAMPLE 5

4-amino-3-[(4-fluorophenyl)amino]-6-phenylpyrazolo[3,4-d]pyrimidine

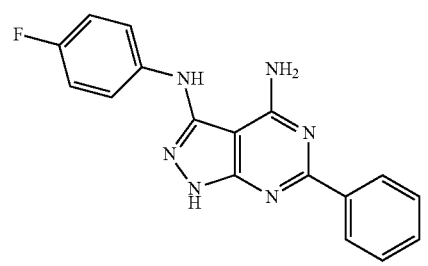

The compound Ref-5 is manufactured in the same way as shown in reference example 2, wherein however 5-amino-4-cyano-3-[(4-fluorophenyl)amino)-pyrazol was used as source material, thereby forming a light yellow crystalline precipitation.

Yield: 70%

Properties: Melting point: 262-263° C. (THF/toluene); MS (m/z): 320 (M'); $^1$H NMR (DMSO-d$_6$): δ 12.69 (1H, s, NH), 8.33-8.41 (4H, m, 4CH), 8.18 (1H, br. s., NH), 7.58-7.65 (5H, m, NH$_2$, 3CH), 7.27-7.31 (2H, n, 2CH) ppm; Elementary analysis C$_{17}$H$_{14}$FN$_6$: Calculated %: C, 63.74; H, 4.09; N, 26.24. Found %: C, 63.81; H, 4.11; N, 26.27.

REFERENCE EXAMPLE 6

4-amino-3-[(3-fluorophenyl)amino]-6-phenylpyrazolo[3,4-d]pyrimidine

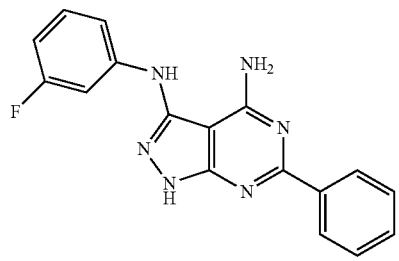

Ref-6

The compound Ref-6 is manufactured in the same way as obtained in reference example 2, wherein however 5-amino-4-cyano-3-[(3-fluorophenyl)amino]-pyrazol was used as source components, thereby forming a light yellow crystalline precipitation.

Yield: 76%

Properties: Melting point: 278-279° C. (THF/toluene); MS (m/z): 320 (M$^+$); $^1$H NMR (DMSO-d$_6$); δ 12.61 (1H, s, NH), 8.34-8.42 (2H, Q, 2CH), 8.14 (1H, br. s., NH), 7.48 (2H, br. s., NH$_2$), 7.3-7.43 (6H, m, 6CH), 6.60 (1H, s, CH) ppm; Elementary analysis for C$_{17}$H$_{14}$FN$_6$: Calculated %: C, 63.74; H, 4.09; N, 26.24. Found %: C, 63.81; H, 4.11; N, 26.27.

EXAMPLE 1

4-amino-3-(4-trifluormethyl-phenyl)amino-6-phenylpyrazolo[3,4-d]pyrimidine (CRCV-340) (6-phenyl-3-N-[4-(trifluormethyl)phenyl]-2H-pyrazolo[3,4-d]pyrimidine-3,4-diamine)

The manufacture was effected as described in reference example 1, using the corresponding substituted precursor compounds.

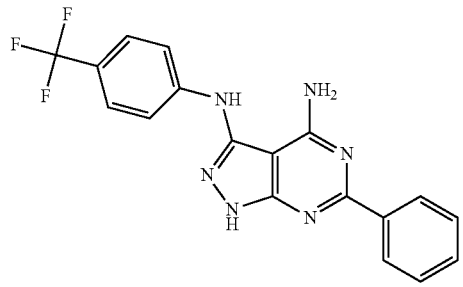

CRCV-340

EXAMPLE 2

4-amino-6-phenyl-3-[(4-(trifluoromethyl)-phenyl] amino-pyrazolo[3,4-d]pyrimidine The compound CRCV-340 was also manufactured analogously to the reaction schedule shown in reference example 2, thereby forming a light yellow crystalline precipitation.

Yield: 58%

Properties: Melting point: 313-314° C. (THF/Toluene); MS (m/z): 370 (M$^+$); $^1$H NMR (DMSO-d$_6$): δ 12.77 (1H, s, NH), 8.91 s, NH), 8.47 (2H, s, NH$_2$), 7.81, 7.79, 7.63, 7.58 and 7.47 (9H, m, C$_6$H$_4$ and C$_6$H$_5$) ppm; Elementary analysis C$_{18}$H$_{13}$F$_3$N$_6$: Calculated %: C, 58.38; H, 3.54; N, 22.69. Found %: C, 58.41; H, 3.58; N, 22.74. HPLC: 99.30% (Säule Luna C18 (2), Acetonitrile/water—90:10, flow of 0.6 ml/min, UV 254 nm; t$_R$=5.3 min)

EXAMPLE 3

4-amino-3-phenylamino-6-[4-(trifluormethoxy)-phenyl]pyrazolo[3,4-d]pyrimidine (MS-112) (3-N-phenyl-6-[4-(trifluormethoxy)phenyl]-2H-pyrazolo[3,4-d]pyrimidine-3,4-diamine)

The manufacture was effected as described in reference example 1 using the correspondingly substituted precursor compounds.

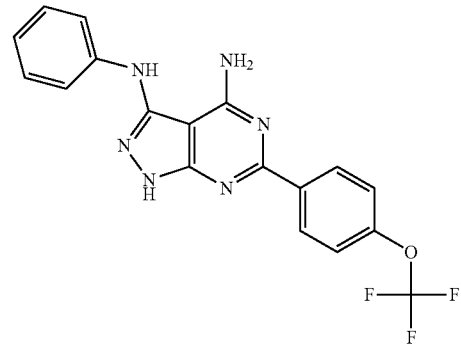

MS-112

EXAMPLE 4

4-amino-6-phenyl-3-[(4-(trifluoromethoxy)-phenylamino]-pyrazolo[3,4-d]pyrimidine This compound was also manufactured analogously to the reaction schedule shown in reference example 2, wherein 5-amino-4-cyano-3-[(4-trifluormethoxyphenyl)amino]pyrazol from source compound was used, thereby forming a white crystalline precipitation.

Yield: 68%

Properties: Melting point: 260-262° C. (tetrahydrofuran/DMF); MS (m/z): 386 (M'); $^1$H NMR (DMSO-d$_6$): δ 12.56 (1H, s, NH), 8.82 (2H, q, 2CH), 8.16 (1H, br. s., NH), 7.48 (2H, br. s., NH$_2$), 7.3-7.43 (4H, m, C$_6$H$_5$), 7.05-7.11 (2H, 2 s, 2CH), 6.98 (1H, m, CH) ppm; Elementary analysis $C_{16}H_{13}F_3N_6O$; Calculated %: C, 55.96; H, 3.39; N, 21.75. Found %: C, 56.07; H, 3.36; N, 21.61.

EXAMPLE 5

Cleaning of 4-amino-6-phenyl-3-[(4-(trifluoromethyl)-phenyl]amino-pyrazolo[3,4-d]pyrimidine 50 g of dry 4-amino-6-phenyl-3-[(4-trifluoromethyl)-phenyl]amino-pyrazolo[3,4-d]pyrimidine, synthesised according to the method described in the reference example 2, is dissolved whilst being warmed in 300 ml of THF. This solution is treated with 300 ml cold toluene. The resulting solution is kept in a freezer at a temperature below 0° C. for a period of 6 hours. 36 g of 4-amino-3-(4-trifluorophenyl)amino-6-phenylpyrazolo[3,4-d]pyrimidine in yellow crystals are obtained by filtration.

Melting point: 313-314° C. (THF/DMF)

HPLC: 99.16% (Säule Luna C18(2), Acetonitrile/water—90:10, flow of 0.6 ml/min, UV 254 nm; $t_R$=5.3 min)

ADMET Studies on the Metabolism of OBR 5-340 In Vitro

Objective: To investigate the Absorption, Distribution, Metabolism, Excretion and Toxicity (abbreviated as: ADMET) of OBR 5-340 in vitro, as well as in vitro tests on the plasma protein binding and the stability in the plasma and in liver microsomes.

Tests: The In vitro tests performed with CRCV-340 as well as the data obtained are summarised in Table 2 in comparison with Ref. 2.

TABLE 2

Summary of the results from the ADMET studies for CRCV-340 in comparison with Ref 2.

| Test parameters | Ref-2 | CRCV-340 |
| --- | --- | --- |
| Binding to plasma protein | 99.5% | 96.7% |
| Release of plasma protein | 61.0% | 122.3% |
| Plasma stability | 117.0% | 100.0% |
| Stability in liver microsomes | 32.0% | 112.0% |

Summary: The substance CRCV-340 is characterized by better stability in liver microsomes as well as an increased release of plasma protein in comparison with Ref-2.

Examination of the Pharmacokinetics of CRCV-340 in Mice

Objective: To collect pharmacokinetic data on CRCV-340.

Tests: Substance and reference substance were applied respectively once in a concentration of 100 mg/kg KG, in 0.5 ml of a 10% Cremophor solution per os to the mice, After 0.5, 1, 2, 3, 4, 5, 6 and 7 hrs serum was taken and by means of HPLC analysis the concentrations of CRCV-340, Ref-2 and Ref-3 determined in the plasma of the mice.

Using the substance concentrations in the blood plasma determined by HPLC the pharmacokinetic parameters of the substances were calculated using the computer program ESTRIP (Table 3).

TABLE 3

Pharmacokinetic data following a single, intragastric application of 100 mg/kg CRCV-340, Ref-2 and Ref-3 in mice.

| Substance | $C_{max}$ (ng/ml) | $T_{max}$ (h) | MRT (h) | $T_{1/2}$ (h) | $K_{el}$ ($h^{-1}$) | CL (ml × h/kg) | $V_d$ (ml/kg) | $AUC_{0-t}$ (ng × ml/h) | $AUC_{0-\infty}$ (ng × ml/h) | $C_{max}/AUC_{0-t}$ ($h^{-1}$) |
| --- | --- | --- | --- | --- | --- | --- | --- | --- | --- | --- |
| Ref-2 | 1295.4 | 1.0 | 2.14 | 2.96 | 0.23 | 36.6 | 156.7 | 2354.5 | 2732.1 | 0.55 |
| Ref-3 | 424.5 | 0.5 | 2.44 | 1.47 | 0.55 | 91.8 | 168.1 | 1085.7 | 1089.4 | 0.39 |
| CRCV-340 | 1254.4 | 3.0 | 3.54 | 3.54 | 0.18 | 10.4 | 52.7 | 6418.3 | 9598.5 | 0.20 |

$C_{max}$ Maximum concentration in the blood
$T_{max}$ Time to reach the maximum concentration in the blood
MRT Mean residence time
$T_{1/2}$ Half life
$K_{el}$ Elimination rate constant
CL Clearance
$V_d$ Volume of distribution
AUC Area under curve
$C_{max}$/AUC Absorption rate from stomach to blood Result: The tests on the pharmacokinetics in mice for CRCV-340 gave a significantly better bioavailability than for Ref-2 and Ref-3.

Tests on Acute Toxicity of CRCV-340 in Mice

Objective: To determine 50% lethal dose of CRCV-340

Tests: The acute toxicity of the substance CRCV-340 was tested in mice 19.5-20.5 g in weight, which was administered per os 40, 60, 80 or 120 mg substance/mouse (per 5 mice per substance and concentration). This corresponds to a dose of approx. 2 g, 3 g, 4 g or 6 g per kilogramme body weight. The toxic effects observed in the result correlated to the substance dose administered. In the 40 and 60 mg/mouse doses up to 3 hrs after the substance was administered coordination disorders and hyperactivity were observed as side effects. Following administration of the two higher doses there were also breathing difficulties, aggressive behaviour and hyperkinesia. For CRCV-340 a $LD_{50}$ of 3120 mg/kg was determined (Table 4).

TABLE 4

Results of the tests on acute toxicity of the substance CRCV-340 after a single peroral administration in mice

| | Dead/Surviving 72 hrs after administration of | |
| --- | --- | --- |
| Dose | Ref-2 | CRCV-340 |
| 40 mg/mouse | 0/5 | 1/5 |
| 60 mg/mouse | 1/5 | 1/5 |
| 80 mg/mouse | 3/5 | 3/5 |

TABLE 4-continued

Results of the tests on acute toxicity of the substance CRCV-340 after a single peroral administration in mice

| | Dead/Surviving 72 hrs after administration of | |
|---|---|---|
| Dose | Ref-2 | CRCV-340 |
| 120 mg/mouse | 4/5 | 5/5 |
| $LD_{50}$ | 78.6 mg/mouse (3930 mg/kg) | 62.4 mg/mouse (3120 mg/kg) |

Result: The data obtained on the survival rate prove very good tolerance of both test substances.

Long Term Studies on the Toxicity in Mice

Objective: To determine the subacute toxicity in mice in order to reveal possible side effects e.g. on general condition, weight, internal organs and metabolism, which could arise with subacute administration of CRCV-340 over 28 days.

Tests: Thus male and female mice weighing approx. 20 g received 12.5, 50 or 200 mg/kg of the substance CRCV-340 in a Cremophor formulation or the control group received Cremophor once a day over 28 days intragastrically administered via a tube. During the total period of the experiment the condition of the coat and the mucous membranes, the excreta and the general condition were assessed. The recording of the weight took place on days 7, 14, 21 and 28. Approx. 24 hrs. after the last substance dose the sense of direction of the animals was examined. The following biochemical parameters in the serum were analysed: protein content, urea, creatinine, the serum activity of aspartate aminotransferase, alanine aminotransferase and alkaline phosphatase. The haemoglobin concentration, hematocrit, the number of red and white blood cells as well as the platelets was determined in the blood smear. At the end of the experiment the mice were killed under anaesthetic and dissected, the condition of the internal organs were assessed macroscopically, the organ weight determined and samples for subsequent histological tests put into formalin.

Results summary: The results prove extremely good tolerance of the substance concentrations examined. Neither the general condition of the animals, their coats, the excreta nor their sense of direction or mobility changed as a result of the substance given. Also in relation to the body weight dynamic the animals treated with CRCV-340 did not differ from the control group. There were no differences between the test groups treated with the substance and the vehicle-treated groups in the blood smear in terms of the biochemical blood parameters. The same applies to the macroscopic assessment of the internal organs (liver, kidney, heart, lung, spleen, pancreas and testes), the weight of the organs as well as the results of the histology tests of the heart, lung, liver, spleen, thymus, pancreas, kidney, gland, testes, stomach and intestinal tissue samples (results not shown).

Determining the Antiviral Spectrum Against Rhinoviruses

Objective: To determine the antiviral effective spectrum of CRCV-340 in respect of 50 different human rhinovirus serotypes and CVB3 patient isolates.

Tests: The 50 HRV serotypes and 20 clinical CVB3 isolates were reproduced in HeLa, HeLa Wis and/or LF cells, their titre determined and the serotype verified using sequencing. Accordingly zpE (zytopathic effect) inhibitory tests with the HRV or plaque-reductions tests with the CVB3 isolates were established. In the corresponding antiviral tests dose effect investigations with Ref-3 and CRCV-340 were carried out. Tables 5 and 6 give an overview of the mean 50% inhibitory concentrations.

TABLE 5

Overview of the effective spectrum of Ref-3 and CRCV-340 in respect of HRV. The mean values and standard deviations for all 50 examined serotypes and for the 45 pleconaril-sensitive and 5 pleconaril-resistant serotypes were summarised separately.

| | $IC_{50}$ [µM] all HRV (n = 50) | | $IC_{50}$ [µM] Pleconaril-sensitive HRV (n = 45) | | $IC_{50}$ [µM] Pleconaril-resistant HRV (n = 5) | | Number of sensitive |
|---|---|---|---|---|---|---|---|
| Substance | mean | S.D. | mean | S.D | mean | S.D. | HRV |
| Ref-3 | 16.11 | 11.94 | 18.52 | 10.88 | 0.07 | 0.01 | 23 |
| CRCV-340 | 25.73 | 21.49 | 26.09 | 18.98 | 22.62 | 40.69 | 49 |

Table 6: Overview of the effective spectrum of Ref-3 and CRCV-340 in respect of the clinical CVB3-isolates. The mean values and standard deviations for all 20 examined isolates and for the 19 pleconaril-sensitive isolates and the one pleconaril-resistant serotype were summarised separately.

| | $IC_{50}$ [µM] all CVB3 (n = 20) | | $IC_{50}$ [µM] Pleconaril-sensitive CVB3 (n = 19) | | $IC_{50}$ [µM] Pleconaril-resistant CVB3 (n = 1) | | Number of sensitive |
|---|---|---|---|---|---|---|---|
| Substance | mean | S. D. | mean | S. D | mean | S.D. | CVB3 |
| Ref-3 | 0.68 | 0.90 | 0.71 | 0.91 | 0.13 | | 20 |
| CRCV-340 | 4.97 | 4.05 | 5.16 | 4.10 | 1.39 | | 18* |

*maximum tested concentration 13.5 µM

Result summary: The effective spectrum of CRCV-340 in respect of HRV was significantly broader in comparison to Ref-3.

Examination of the Antiviral Effect In Vivo in the Mouse model of CVB3-Induced Chronic Myocarditis Objective: To confirm the antiviral effect of CRCV-340 in the mouse model Investigations: The effect of CRCV-340 was investigated in the model of CVB 3-induced myocarditis in 8-week old male NMRI mice. In addition CVB3 31-1-93 or CVB3 H3-infected animals received once or twice a day 100 mg/kg of the substance in 50% or 20% PEG-400 in 1% CMC in water (placebo) administered over 7 days. Parameters to evaluate the therapeutic effect included changes in body weight, general condition, virus titre in heart and pancreas tissue as well as histopathological changes in the heart and pancreas. Pseudo-infected, placebo-treated or CRCV-340-treated animals served as a negative control and infected, placebo- or pleconaril-treated animals as a positive control over the course of the infection.

Result summary: in contrast to the placebo and pleconaril CRCV-340 was effective in the model of the CVB3 31-1-93-induced chronic myocarditis in NMRI-mice. In the process clinically and statistically significant effects for all examined parameters (body weight, general condition, the virus titre in the heart and pancreas tissue on day 7 p.i., the histopathology in the heart and pancreas on day 7 and 21 p.i.) were observed.

Studies on the In Vivo Effectiveness of CRCV-340 in the Lethal Mouse Model Compared to the Reference Substance Pleconaril Objective: To verify the antiviral effect of CRCV-340 in the lethal mouse model Investigations: The effect of the development candidate CRCV-340 was examined following testing of the infection dose in the model of the CVB 3-induced myocarditis in 6-7 weeks old male BALB/c mice. In addition CVB3 31-1-93 or CVB3 H3-infected animals received twice a day 100 mg/kg of the substance in 20% PEG-400 in 1% CMC in water (placebo) administered over 7 days. Changes in body weight, general condition and the lethality defined through the surrogate marker 25% loss of body weight served as parameters to evaluate the therapeutic effect. Pseudo-infected, placebo-treated or CRCV-340-treated animals represented the negative control and infected, placebo- or pleconaril-treated animals the positive control over the course of the infection.

Result summary: In contrast to the placebo and pleconaril CRCV-340 was effective in the lethal BALB/c mouse model after infection with CVB3 31-1-93. In the process clinically and statistically significant effects for all examined parameters (body weight, general condition as well as lethality) were observed.

The invention claimed is:

1. A 4-amino-3-phenylamino-6-phenylpyrazolo[3,4-d]pyrimidine of formula IIa

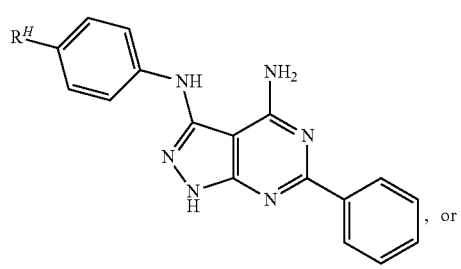

IIa

, or

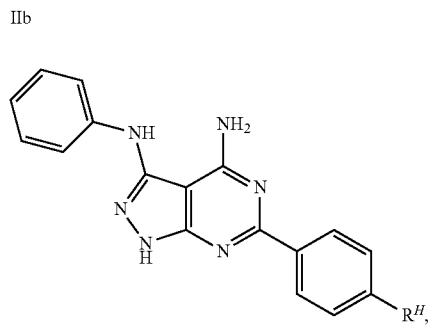

IIb or a pharmaceutically acceptable salt or pro-pharmacon thereof, wherein $R^H$ is $NO_2$, CN, $CF_3$, $CCl_3$, $CBr_3$, $OCF_3$, $OCCl_3$, $OCBr_3$, $CHF_2$, $CHCl_2$, $CHBr_2$, $OCHCl_2$, CHO, COOH, COMe, COEt, COOMe or COOEt.

2. The 4-amino-3-phenylamino-6-phenylpyrazolo[3,4-d]pyrimidine according to claim 1 of the formula

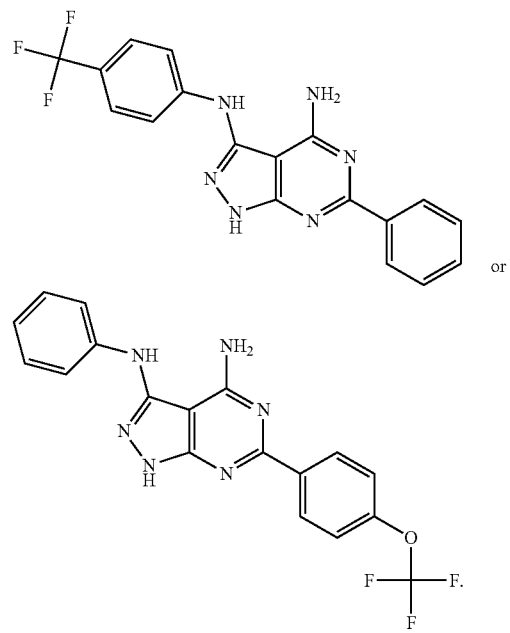

or

3. A pharmaceutical composition, comprising a 4-amino-3-phenylamino-6-phenylpyrazolo[3,4-d]pyrimidine according to claim 1.

4. The pharmaceutical composition according to claim 3, also comprising a pharmaceutically acceptable carrier.

5. The pharmaceutical composition according to claim 3, also comprising one or several other active ingredients.

6. The pharmaceutical composition according to claim 5, wherein the one or the several other active ingredients are antiviral agents.

7. A method to manufacture a pharmaceutical composition, comprising combining a 4-amino-3-phenylamino-6-phenylpyrazolo[3,4-d]pyrimidine according to claim 1 with a pharmaceutically acceptable carrier.

8. A method for therapeutic treatment of picornavirus infections in an animal in need thereof, comprising administering to said animal an effective amount of a 4-amino-3-phenylamino-6-phenylpyrazolo[3,4-d]pyrimidine according to claim 1, wherein the picornavirus infections are rhinovirus or enterovirus infections.

9. A method to manufacture a 4-amino-3-phenylamino-6-phenylpyrazolo[3,4-d]pyrimidine according to claim 1, comprising reacting a 5-amino-4-cyano-3-phenylaminopyrazol with the free base of a benzamidine in a polar organic solvent.

10. The method according to claim 9, wherein the 4-amino-3-phenylamino-6-phenylpyrazolo[3,4-d]pyrimidine is purified by recrystallization using tetrahydrofuran or a mixture thereof with water or an organic solvent or by precipitation using a hot solution in tetrahydrofuran with water or an organic solvent.

11. The 4-amino-3-phenylamino-6-phenylpyrazolo[3,4-d]pyrimidine according to claim 1, characterized by the fact that $R^H$ is $CF_3$ or $OCF_3$.

12. The pharmaceutical composition according to claim 6, wherein the one or the several other active ingredients are active agents against picornaviruses.

13. The method according to claim 9, wherein the polar organic solvent is n-butanol.

14. The method according to claim 10, wherein the organic solvent is toluene.

* * * * *

UNITED STATES PATENT AND TRADEMARK OFFICE
CERTIFICATE OF CORRECTION

PATENT NO. : 9,790,225 B2  
APPLICATION NO. : 14/350885  
DATED : October 17, 2017  
INVENTOR(S) : Wutzler et al.

Page 1 of 1

It is certified that error appears in the above-identified patent and that said Letters Patent is hereby corrected as shown below:

On the Title Page

Item (30) Foreign Application Priority Data: Please correct:
"10 2011 116 373" to read -- 10 2011 116 373.9 --
"10 2011 116 384" to read -- 10 2011 116 384.4 --

In the Specification

Column 4, Line 19: Please correct:
"COON" to read -- COOH --

Column 5, Line 29: Please correct:
"COON" to read -- COOH --

Column 13, Line 62: Please correct:
"(DMSO-$d_e$)" to read -- (DMSO-$d_6$) --

Signed and Sealed this
Twenty-sixth Day of June, 2018

Andrei Iancu
*Director of the United States Patent and Trademark Office*